United States Patent
Pacino, Jr. et al.

(10) Patent No.: US 6,508,646 B2
(45) Date of Patent: Jan. 21, 2003

(54) SECURABLE MOUNTING FOR AN ARTICULATOR FOR DENTAL CASTS

(75) Inventors: Nicholas R. Pacino, Jr., St. Louis, MO (US); Terry L. Jackson, St. Louis, MO (US)

(73) Assignee: J & P Group, LLC, St. Louis, MO (US)

(*) Notice: Subject to any disclaimer, the term of this patent is extended or adjusted under 35 U.S.C. 154(b) by 0 days.

(21) Appl. No.: 09/916,950

(22) Filed: Jul. 27, 2001

(65) Prior Publication Data

US 2002/0146661 A1 Oct. 10, 2002

Related U.S. Application Data

(63) Continuation-in-part of application No. 09/826,184, filed on Apr. 4, 2001.

(51) Int. Cl.[7] ............................................. A61C 11/00
(52) U.S. Cl. ........................................... 433/64; 433/60
(58) Field of Search ......................... 433/60, 57, 58, 433/59, 61, 62, 63, 64, 65, 66, 67

(56) References Cited

U.S. PATENT DOCUMENTS

| | | | | | |
|---|---|---|---|---|---|
| 2,621,407 | A | * | 12/1952 | Schlesinger | 433/57 |
| 4,533,323 | A | * | 8/1985 | Huffman | 433/60 |
| 4,548,581 | A | * | 10/1985 | Huffman | 433/64 |
| 4,797,097 | A | * | 1/1989 | Cohn | 433/64 |
| 5,425,636 | A | * | 6/1995 | Ghim | 433/64 |

* cited by examiner

*Primary Examiner*—John J. Wilson
(74) *Attorney, Agent, or Firm*—Polster, Lieder, Woodruff & Lucchesi, L.C.

(57) ABSTRACT

A mounting for being mounted to a dental cast and for receiving a ball portion of an articulator, the mounting comprising a tongue portion connected to a wall portion, the tongue portion adapted to being mounted to a dental cast, a cup portion being formed by a side connected to the wall portion, an opening formed in the side, and a fastening device for insertion through the opening for engagement with a ball portion of an articulator for securing a ball portion in place relative to the mounting.

17 Claims, 1 Drawing Sheet

US 6,508,646 B2

SECURABLE MOUNTING FOR AN ARTICULATOR FOR DENTAL CASTS

CROSS REFERENCE TO RELATED APPLICATIONS

This application is a continuation-in-part of prior U.S. patent application Ser. No. 09/826,184 which was filed on Apr. 4, 2001.

BACKGROUND OF THE INVENTION

This invention relates to a mounting for an articulator used in conjunction with dental casts, and more particularly, to a mounting for an articulator for dental casts which can be secured to the articulator.

Articulators are used in conjunction with casts of a dental model in order for a technician to develop, construct, or form prosthetic dentures or other denture elements. A dentist makes the dental casts of both the upper and lower jaws of a patient by using any well known casting methods. The technician uses these casts to shape or fit the denture elements in order to correct any dental problems. The articulator is attached to both of the dental casts by use of mountings. Once attached, the articulator is used to simulate the movement of the jaws relative to each other and the technician uses this movement to confirm proper registration or fit of the denture elements. It is important for the articulator to be able to allow the casts to move in all directions in order for the technician to verify the correctness of the dentures. For example, the articulator needs to be able to allow movement of the casts in order to confirm the registration of all opposed dental surfaces. Articulators have been constructed or formed of different materials and different details of construction. Known articulators range from simple designs to complex mechanical designs. Such articulators also range in price from inexpensive to expensive.

Additionally, the mountings are connected to the dental casts with the mountings having a socket portion of a ball and socket joint. The articulators typically have the ball portion which fits into the socket portion associated with the mountings. In this manner, the articulator is able to move relative to the dental casts. Once it is determined that the dental elements have successful registration, any movement of the articulator relative to the mountings should be fixed. Typically, the ball portions of the articulator are bonded to the socket portions of the mountings by use of an adhesive or glue. However, this method is unacceptable for several reasons. One reason is that when gluing the portions together the dental casts may come out of alignment or registration. Another reason is that once glued, if realignment or further adjustment is required then the mountings and the articulator must be destroyed.

The present invention is designed to obviate and overcome many of the disadvantages and shortcomings associated with presently available methods and constructions of fixing or securing mountings relative to articulators. In particular, the present invention is a mounting for an articulator which is designed and constructed to be secured to the articulator and also capable of being disassembled or reused. Moreover, the securable mounting of the present invention can be employed to construct dental devices and to register such devices in an accurate manner and alignment.

SUMMARY OF THE INVENTION

In one form of the present invention, a mounting for being mounted to a dental cast and for receiving a ball portion of an articulator comprises a tongue portion connected to a wall portion, the tongue portion adapted to being mounted to a dental cast, a cup portion being formed by a side connected to the wall portion, an opening formed in the side, and a fastening device for insertion through the opening for engagement with a ball portion of an articulator for securing a ball portion in place relative to the mounting.

In another form of the present invention, a mounting for connection to a dental cast and for receiving a ball portion of an articulator comprises a wall portion having a tongue portion extending therefrom, the tongue portion for being positioned in a dental cast, a socket portion being formed by a side extending from the wall portion, an opening formed in the side, and a securing device for insertion into the opening.

In yet another form of the present invention, a mounting for connection to a dental cast and an articulator with the articulator having a ball portion with the ball portion having an aperture, the mounting comprising a wall portion having a tongue portion extending therefrom, the tongue portion for being positioned in a dental cast, a socket portion being formed by a side extending from the wall portion with the socket portion for receiving the ball portion, an opening formed in the side with the opening being aligned with the aperture in the ball portion, and a securing device for insertion through the opening and into the aperture of the ball portion.

In light of the foregoing comments, it will be recognized that a principal object of the present invention is to provide a mounting that may be secured to an articulator.

A further object of the present invention is to provide a mounting which is of simple construction and design and which can be easily employed with highly reliable results.

Another object of the present invention is to provide a mounting that is easy to use and may be moved or operated through a large degree of motion or movement.

A still further object of the present invention is to provide a mounting that can be secured to and released from an articulator.

A further object of the present invention is to provide a mounting which may be used with an articulator to prepare and construct a dental appliance or restoration.

Another object of the present invention is to provide a mounting which may be secured to an articulator which simulates jaw movement in order for a technician to construct a dental appliance and to verify proper alignment of the dental appliance.

A further object of the present invention is to provide a mounting that is strong and flexible and has unitary construction.

Another object of the present invention is to provide a mounting which may be easily repositioned relative to an articulator.

These and other objects and advantages of the present invention will become apparent after considering the following detailed specification in conjunction with the accompanying drawings, wherein:

DETAILED DESCRIPTION OF THE PREFERRED EMBODIMENTS

Figure 1:
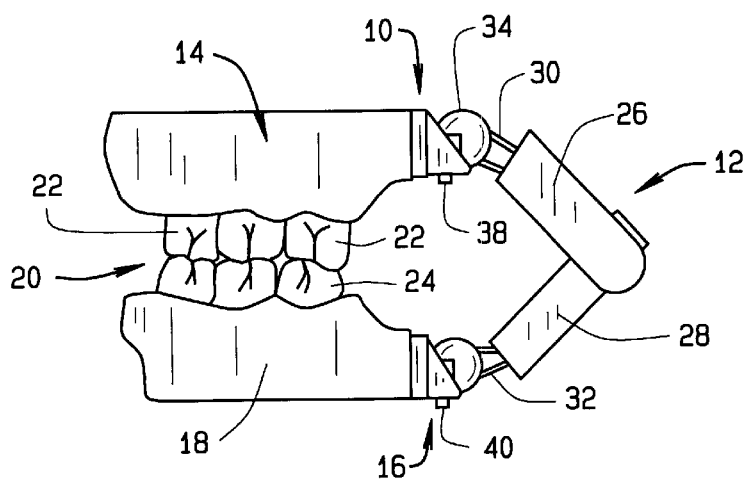
FIG. 1 is a side view of a preferred embodiment of a pair of mountings for an articulator constructed according to the present invention with the pair of mountings being mounted to a pair of dental molds.

Referring now to the drawings, wherein like numbers refer to like items, number 10 identifies a preferred embodiment of a mounting 10 for an articulator 12 constructed according to the present invention. With reference now to FIG. 1, the mounting 10 is shown mounted to a first or upper dental cast 14. A second mounting 16 is also shown mounted to a second or lower dental cast 18. The dental casts 14 and 18 are used to simulate a mouth 20, such as a person who needs to have dentures or other dental appliances. The mouth 20 can include teeth 22 which simulate the teeth of a person. Additionally, the mouth 20 may have a tooth 24 which may be a prosthetic or false tooth composed of a synthetic material such as gold or porcelain. The tooth 24 must be configured and shaped to naturally mate with or align with the tooth 22. The tooth 22 may be a simulation of an actual tooth in the mouth of a person with which the tooth 24 must contact. The casts 14 and 18 may be formed of any known casting material used for making such casts 14 and 18. Further, the teeth 22 are cast from the same material. Also, the mouth 20 may have more than one tooth 24 which needs to be constructed or fabricated for an individual.

The articulator 12 is shown to be comprised of a pair of interconnecting members 26 and 28 that are positioned within the pair of mountings 10 and 16, respectively. Each of the members 26 and 28 has a spline portion 30 and 32, respectively. A ball 34 is connected to the spline 30 and a ball 36 is connected to the spline 32. The mountings 10 and 16 are sized and shaped to receive the balls 34 and 36. In this manner, the members 26 and 28 are free to move or rotate within the mountings 10 and 16. The mountings 10 and 16 each further comprise a fastening or securing device 38 and 40, respectively, such as a screw, set screw, or thumb screw. As will be explained, the securing devices 38 and 40 are used to secure the members 26 and 28 of the articulator 12 relative to the mountings 10 and 16.

As can be appreciated, the casts 14 and 18 in conjunction with the articulator 12 and the mountings 10 and 16 may be moved relative to each other in order to simulate the movement of a person's jaws. By use of the articulator 12, the tooth 24 can be viewed to determine if the tooth 24 will impact or mate with the tooth 22 in order for a technician to verify the correctness of the fit of the tooth 24. If it is determined that the teeth 22 and 24 are not mating correctly, then the technician can make adjustments or alterations to the tooth 24. The articulator 12 also allows the technician to move or rotate either of the casts 14 or 18 apart from each other in order to view the tooth 24.

Figure 2:
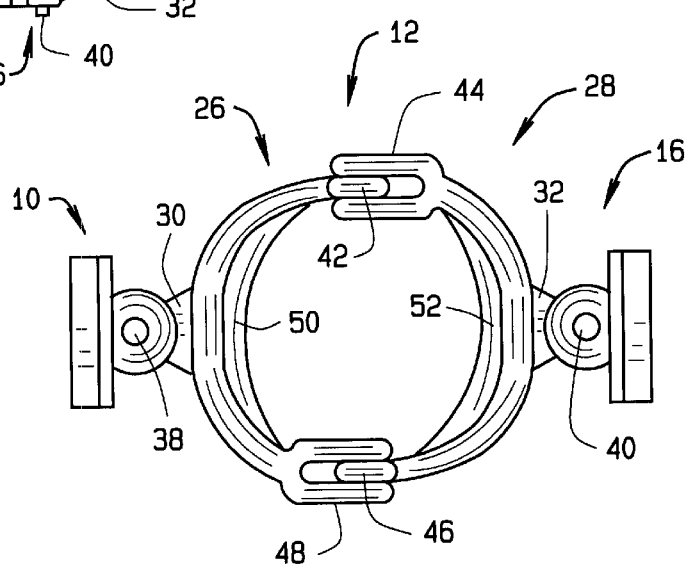
FIG. 2 is a top view of the pair of mountings of the present invention with an articulator being positioned on the pair of mountings.

With reference now to FIG. 2, the members 26 and 28 are shown connected together to form the articulator 12. As is shown, a first end 42 of the member 26 is connected to or hooked onto a second end 44 of the member 28. Further, a first end 46 of the member 28 is connected to a second end 48 of the member 26. The mounting members 10 and 16 are shown receiving the balls 34 and 36 of the respective members 26 and 28 as is evidenced by the splines 30 and 32. The securing devices 38 and 40 are also shown being inserted into the mountings 10 and 16. Each of the members 26 and 28 has a reinforcing rib 50 and 52, respectively.

Figure 3:
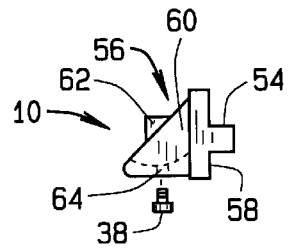
FIG. 3 is a side view of a mounting for an articulator for dental casts constructed according to the present invention.

With particular reference now to FIG. 3, the mounting 10 is shown to have a tongue 54 and a cup portion 56. The tongue 54 is connected to a wall portion 58. The tongue 54 and the wall portion 58 are T-shaped. The tongue 54 is adapted to being inserted into a groove that is formed in the dental cast 14 for mounting the dental cast 14 to the mounting 10. The mounting 10 further comprises a side 60 with the side 60 having a pair of extensions 62, one of which is visible, which are used to help retain the ball 34 (not shown) when the ball 34 is seated within the cup portion 56. The side 60 is integrated with the wall 58 with both the wall 58 and the side 60 forming the cup portion 56. The mounting 10 further comprises an aperture or opening 64 which is adapted for receiving the securing device 38. The opening 64 may be threaded and the securing device 38 may also be threaded. In this manner, the securing device 38 is screwed into the opening 64. Further, when the securing device 38 is inserted into the opening 64, the device 38 will contact the ball 34 to prevent movement of the ball 34. Loosening of the securing device 38 will allow movement of the ball 34 relative to the mounting 10. The mounting 10 may be constructed of the same material of which the members 26 and 28 are constructed. Further, the mounting 16 is identical to the mounting 10.

Figure 4:
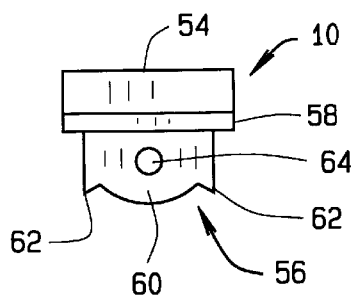
FIG. 4 is a top view of the mounting shown in FIG. 3.

FIG. 4 depicts a top view of the mounting 10. Again, the mounting 10 is shown to have the tongue 54 and the cup portion 56. The tongue 54 is connected to a wall portion 58. The tongue 54 and the wall portion 58 are T-shaped. The mounting 10 further comprises the side 60 with the side 60 having the pair of extensions 62 which are used to help retain and support the ball 34 (not shown) when the ball 34 is seated within the cup portion 56. The side 60 is integrated with the wall 58 with both the wall 58 and the side 60 forming or defining the cup portion 56. The mounting 10 further comprises the aperture or opening 64 which is adapted for receiving the securing device 38. The opening 64 may be threaded and the securing device 38 may also be threaded.

Figure 5:
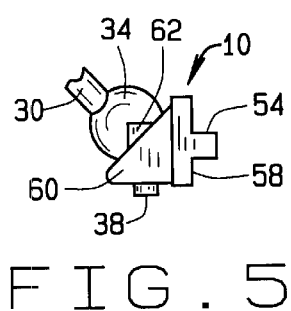
FIG. 5 is a side view of the mounting shown in FIG. 3 with a portion of an articulator inserted therein.

Referring now to FIG. 5, the mounting 10 is shown to have the ball 34 inserted into the mounting 10. The securing device 38 has also been inserted into the mounting 10 to secure or lock the ball 34 in place. As indicated previously, once the securing device 38 is loosened the ball 34 is free to move within the cup portion 56 or be removed entirely from the mounting 10. Additionally, tightening of the securing device 38 prevents any movement of the ball 34 relative to the mounting 10. In this manner, the mounting 10 may be tightened or loosened any number of times as required.

Figure 6:
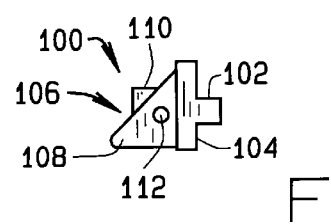
FIG. 6 is a side view of another preferred embodiment of a mounting for an articulator for dental casts constructed according to the present invention.

FIG. 6 illustrates another preferred embodiment of a mounting 100 of the present invention. The mounting 100 comprises a tongue portion 102 connected to a wall portion 104 with the tongue portion 102 and the wall portion 104 being T-shaped. The tongue portion 102 can be placed into a groove that may be formed in the dental cast, for example the dental casts 14 or 18. The mounting 100 further comprises a socket portion 106 being formed from a cup shaped side 108 and the wall 104. The side 108 has a pair of extensions 110, one of which is shown, which is employed to retain and support a ball, such as the balls 34 or 36, when a ball is inserted into the socket portion 106. The mounting 100 further comprises an opening 112 which is adapted to receive a fastening device (not shown), such as the fastening or securing devices 38 or 40. The opening 112 may be a threaded opening and the securing device may also be threaded to allow the securing device to be selectively tightened or loosened. One main difference between mountings 10 and 16 versus the mounting 100 is the position or placement of the opening 112 on the side 108. It is also possible to have a second opening or a series of openings along the side 108.

Figure 7:
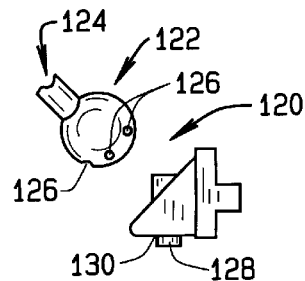
FIG. 7 is a side view of another preferred embodiment of a mounting for an articulator for dental casts constructed according to the present invention.

With reference now to FIG. 7, another preferred embodiment of a mounting 120 is shown. In particular, the mounting 120 is identical to either the mountings 10 or 16 with a principal difference being that a ball 122 associated with an articulator 124 has one or more apertures or openings 126 formed along the ball 122. The apertures 126 are used to position or orientate the articulator 124 within the mounting 120. With the use of the apertures 126, the position or orientation of the articulator 124 may be selected or calibrated if required. By using a fastening device 128 inserted through an opening 130 of the mounting 120 and into one of the apertures 126, the ball 122 may be secured in place. It is also contemplated that a mounting, such as the mounting 100, may be used with the ball 122. Further, a mounting having a series of openings which match or line up with the apertures 126 of the ball 122 may also be used. In this manner, a number of securing devices may be used. Although the ball 122 is shown and described as having the apertures 126, it is also possible that the ball 122 may have a groove instead of the apertures 126 with the groove for receiving the fastening device 128.

As can be appreciated from the above, the dental casts 14 and 18, when mounted to the articulator 12 can be easily moved or positioned with respect to each other. A technician can manipulate the casts 14 and 18 to rotate, move, or position the casts 14 and 18 in any desired direction or position for reviewing the dental appliance 24 associated with the casts 14 and 18. Once the proper alignment of the dental appliance 24 is accomplished, the fastening devices 38 and 40 may be used to lock or secure the ball portions 34 and 36 in place. Additionally, if required, the fastening devices 38 and 40 may be loosened and retightened many times. As can be appreciated, there is no need to use glue or other adhesives to secure the articulator 12 in place. Further, the articulator 12 and the mounting 10 mounted to the casts 14 and 16 may be shipped or transported back to a dentist for manipulation or confirmation by the dentist.

It should be recognized that the mountings 10, 100, and 120 of the present invention could be constructed of various materials. Preferably, the mountings 10, 100, and 120 will be of relatively lightweight material so that they can be easily constructed, assembled, positioned, secured in place, and removed. Further, the mounting 10, 100, and 150 will be constructed of relatively inexpensive materials which will provide for the mountings 10, 100, and 150 to be disposable or suitable for one time use.

From all that has been said, it will be clear that there has thus been shown and described herein a mounting which fulfills the various objects and advantages sought therefor. It will become apparent to those skilled in the art, however, that many changes, modifications, variations, and other uses and applications of the subject mounting are possible and contemplated. All changes, modifications, variations, and other uses and applications which do not depart from the spirit and scope of the invention are deemed to be covered by the invention, which is limited only by the claims which follow.

What is claimed is:

1. A mounting for being mounted to a dental cast and for receiving a ball portion of an articulator, the ball portion having an aperture, the mounting comprising a tongue portion connected to a wall portion, the tongue portion adapted to being mounted to a dental cast, a cup portion being formed by a side connected to the wall portion, an opening formed in the side, and a fastening device for insertion through the opening for engagement with the aperture of the ball portion for securing the ball portion in place relative to the mounting.

2. The mounting of claim 1 wherein the ball portion comprises a second aperture and the mounting further comprises a second opening formed in the side and a second fastening device for insertion through the second opening for engagement with the second aperture of the ball portion.

3. The mounting of claim 1 wherein the opening is threaded.

4. The mounting of claim 3 wherein the fastening device is threaded and adapted to be threaded into the threaded opening.

5. The mounting of claim 1 wherein the ball portion comprises a series of apertures and the mounting further comprises a series of openings formed in the side and a series of fastening devices for insertion through the series of openings for engagement with the series of apertures of the ball portion.

6. The mounting of claim 1 wherein the side has a top and the opening is located in the top.

7. A mounting for connection to a dental cast and for receiving a ball portion of an articulator, the ball portion having a groove, the mounting comprising a wall portion having a tongue portion extending therefrom, the tongue portion for being positioned in a dental cast, a socket portion being formed by a side extending from the wall portion, an opening formed in the side, and a securing device for insertion into the opening and for engagement with the groove.

8. The mounting of claim 7 further comprises a second opening formed in the side and a second fastening device for insertion through the second opening and for engagement with the groove.

9. The mounting of claim 7 wherein the securing device is a screw.

10. The mounting of claim 7 wherein the opening is threaded and the securing device is threaded.

11. The mounting of claim 7 further comprises a series of openings formed in the side and a series of securing devices for insertion through the series of openings and for engagement with the groove.

12. The mounting of claim 7 wherein the side has a top and the opening is located in the top.

13. The mounting of claim 7 wherein the securing device is a set screw.

14. A mounting for connection to a dental cast and an articulator with the articulator having a ball portion with the ball portion having an aperture, the mounting comprising a wall portion having a tongue portion extending therefrom, the tongue portion for being positioned in a dental cast, a socket portion being formed by a side extending from the wall portion with the socket portion for receiving the ball portion, an opening formed in the side with the opening being aligned with the aperture in the ball portion, and a securing device for insertion through the opening and into the aperture of the ball portion.

15. The mounting of claim 14 wherein the ball portion has a second aperture and the side further comprises a second opening with the second opening being aligned with the second aperture in the ball portion.

16. The mounting of claim 14 wherein the ball portion has a series of apertures and the side further comprises a series of openings with the series of openings being aligned with the series of apertures in the ball portion.

17. The mounting of claim 14 wherein the opening is threaded and the securing device is threaded.

* * * * *